United States Patent [19]

Dotson, Jr.

[11] Patent Number: 4,609,368

[45] Date of Patent: Sep. 2, 1986

[54] PNEUMATIC ULTRASONIC SURGICAL HANDPIECE

[76] Inventor: Robert S. Dotson, Jr., 119 Amanda Dr., Oak Ridge, Tenn. 37830

[21] Appl. No.: 643,252

[22] Filed: Aug. 22, 1984

[51] Int. Cl.⁴ .............................................. A61B 17/20
[52] U.S. Cl. ........................................ 604/22; 604/27; 604/35; 128/24 A; 128/305
[58] Field of Search ............................ 604/22, 28–35, 604/23, 27, 118–121; 128/303 C, 305, 24 A, 328, 303 R

[56] References Cited

U.S. PATENT DOCUMENTS

| 3,994,297 | 11/1976 | Kopf | 604/22 |
| 4,314,560 | 2/1982 | Helfgott et al. | 604/35 |
| 4,428,748 | 1/1984 | Peyman et al. | 604/22 |

Primary Examiner—Dalton L. Truluck
Assistant Examiner—Mario Costantino
Attorney, Agent, or Firm—Pitts and Brittian

[57] ABSTRACT

A surgical handpiece having an ultrasonically driven tool operated by gas under pressure. A surgical handpiece useable for ophthalmic and other microsurgery uses a whistle for generating ultrasonic waves and causing a driving member to reciprocate at ultrasonic frequency. The handpiece has a probe with a needle or other tool reciprocable within the probe. Irrigation liquid can be supplied through the handpiece and through the probe, surrounding the tool to remove heat. The tool has a lumen, and the lumen is connected to a source of vacuum through the handpiece for aspiration of tissue fragmented by the reciprocating tool.

12 Claims, 5 Drawing Figures

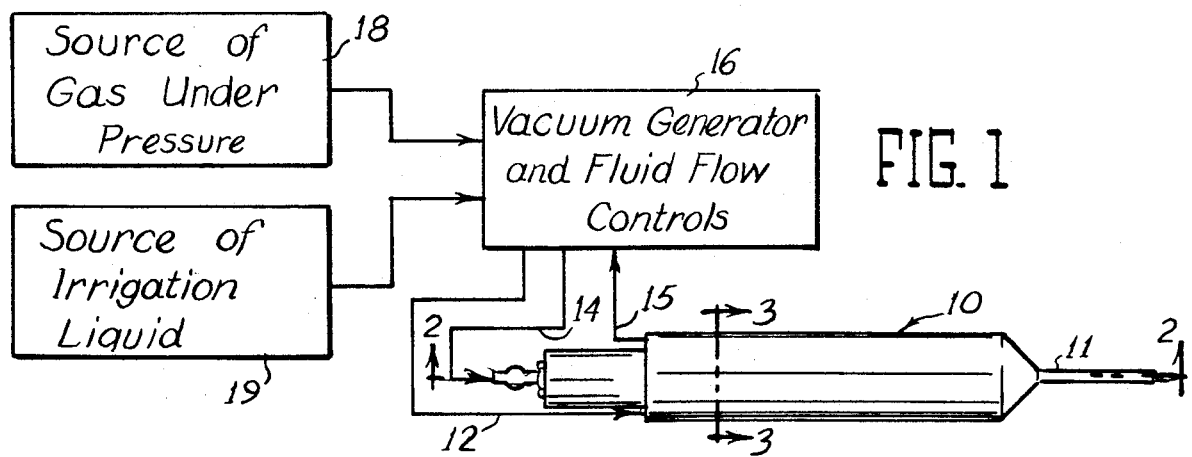
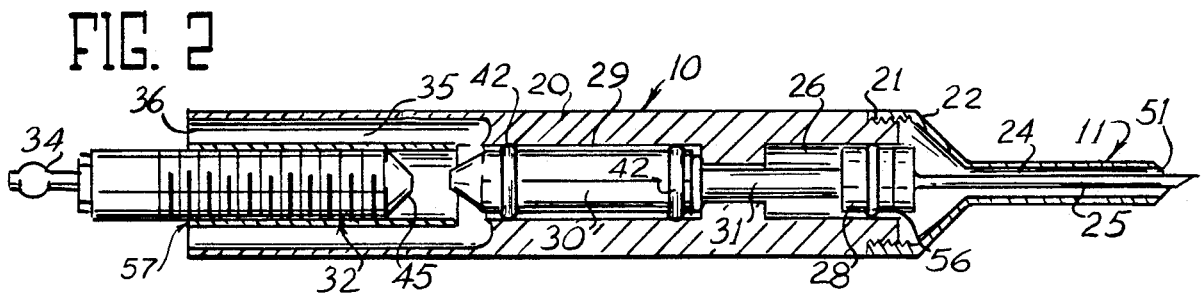
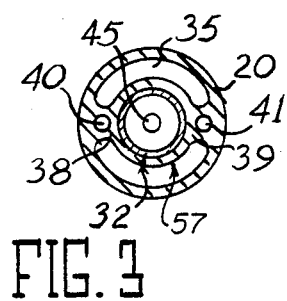
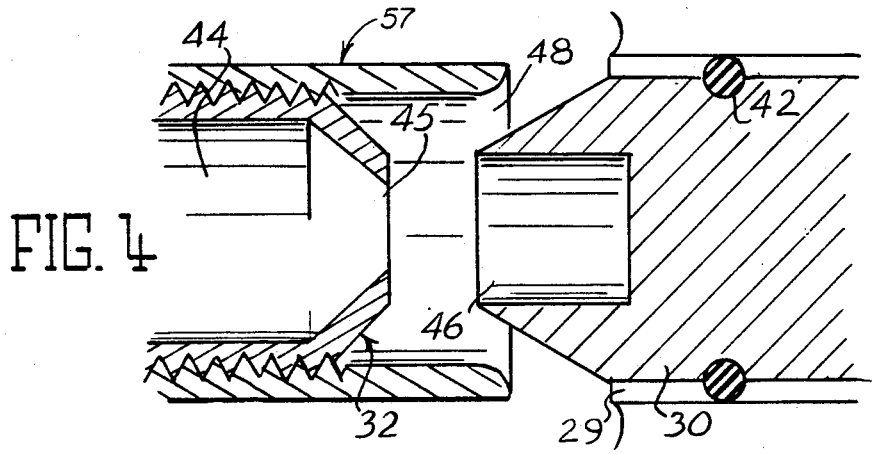
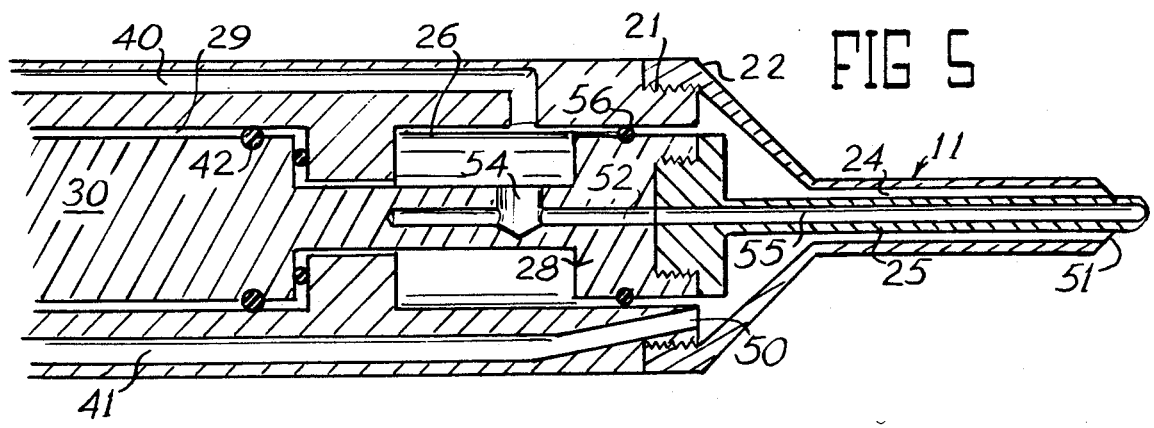

PNEUMATIC ULTRASONIC SURGICAL HANDPIECE

INFORMATION DISCLOSURE STATEMENT

It is known to use ultrasonic vibrations in various surgical procedures, wherein the ultrasonic waves drive a tool in order to perform some operation. These ultrasonic devices usually utilize electrical means for producing the ultrasonic waves, and thus require the presence of electrical power to operate the instruments. Also, the necessity of using electrical energy renders the apparatus quite complex; and, of course heat is generated and must be dissipated in some manner. In many of the extremely delicate operations, such as ophthalmic surgery, it will be understood that generation of excess heat can be hazardous to the patient.

In any surgical equipment, it is desirable that the equipment be capable of sterilization in an autoclave. Since sterilization by gas requires at least 24 hours, permanent equipment is out of service a long time if gas sterilization is required. Of course, disposables can be sterilized by gas because the disposables would normally be sterilized, and packaged in a sterile condition for a one-time use. It will be understood that complex electrical and electronic equipment is frequently unable to withstand the temperatures necessary for autoclaving, and this is a severe problem.

SUMMARY OF THE INVENTION

This invention relates generally to an ultrasonically driven surgical handpiece, and is more specifically concerned with a surgical handpiece for use with a pneumatic system wherein all functions are controlled by a gas under pressure.

The present invention provides a surgical handpiece for use in ophthalmic surgery and the like, the handpiece including a probe carried at one end thereof. The probe may be hollow to carry a reciprocating needle. The needle is mechanically attached to ultrasonic generating means such as to a cup that forms part of a whistle, the cup being vibrated for causing reciprocation of the needle. The nozzle portion of the whistle is carried at the opposite end of the handpiece, and is held with respect to the cup at a pre-selected distance to determine the rate of oscillation of the cup. In the preferred embodiment of the invention, the handpiece is designed specifically for ophthalmic use and the diameter of the probe and needle is of such size as to be appropriate for ophthalmic surgery. A supply of irrigation liquid is provided to the handpiece, and the irrigation liquid passes between the probe and the needle for both maintaining pressure within the eye and assisting in cooling the probe. A vacuum source is applied through a lumen in the needle for aspirating tissue.

BRIEF DESCRIPTION OF THE DRAWINGS

These and other features and advantages of the present invention will become apparent from consideration of the following specification when taken in conjunction with the accompanying drawings in which:

FIG. 1 is an elevational view of a handpiece made in accordance with the present invention, and schematically showing control apparatus;

FIG. 2 is an enlarged cross-sectional view taken substantially along the line 2—2 in FIG. 1;

FIG. 3 is an enlarged cross-sectional view taken substantially along the line 3—3 in FIG. 1;

FIG. 4 is an enlarged cross-sectional view through the whistle shown in FIG. 2; and, FIG. 5 is an enlarged, longitudinal cross-sectional view through the probe end of the handpiece shown in FIGS. 1 and 2.

DETAILED DESCRIPTION OF THE EMBODIMENT

Referring now more particularly to the drawings, and to that embodiment of the invention here presented by way of illustration, FIG. 1 shows a handpiece generally designated at 10 having a probe 11 at one end thereof. The opposite end contains fluid connections including a line 12 for providing irrigation liquid, a line 14 for providing gas under pressure, and a line 15 for aspiration. The lines 12, 14 and 15 are connected to a control unit designated at 16. The control unit 16 is in turn connected to a source of gas under pressure designated at 18 and a source of irrigation liquid designated at 19.

Those skilled in the art will understand that control apparatus such as that indicated at 16 is known, and is disclosed in applicant's U.S. Pat. No. 4,274,411 issued June 23, 1981. While that patent discloses an operable device, the present invention may be operated from other equipment, so long as the appropriate controls are available to the surgeon for operation of the handpiece of the present invention.

Looking now at FIG. 2 of the drawings, it will be seen that the handpiece 10 includes a generally cylindrical housing designated at 20, the body 20 defining threads 21 at one end thereof for receiving the enlarged end 22 of the probe 11. It will also be seen that the probe 11 includes a central passageway 24 for receiving the needle 25.

The forward end of the body 20 also defines a bore 26 to receive the tool driving member 28, the needle 25 being removably fixed to the driving member 28 as will be discussed hereinafter.

Generally centrally of the body 20, there is another bore designated at 29, the bore 29 containing the cup carrying member 30. It will be seen that the member 30 is connected to the driving member 28 through a stem 31.

The rear end of the body 20 carries the nozzle 32 of the whistle, or sound generating means, threadably received in a centrally disposed sleeve 57. It will be seen in FIG. 2 that the nozzle 32 includes a generally conventional hose connection 34 at its rearmost end so that gas under pressure can be directed into the nozzle 32. Gas will exit from the righthand end of the nozzle 32 to be directed into the cup of the member 30. Gas can then escape through the passages 35 to be discharged at the opening 36.

The construction of the rear end of the body 20 is shown in FIG. 3 where it will be seen that the nozzle 32 is located generally centrally of the body 20, and the passages 35 are located at each side of the nozzle 32. Web portions 38 and 39 remain between the passages 35, and these web portions 38 and 39 define passageways 40 and 41 therethrough. The passageways 40 and 41 allow connection of the tubings 12 and 15 as was discussed in connection with FIG. 1 of the drawings, and the internal connections of these passages 40 and 41 will be discussed in more detail below.

Considering now the generator for the sound waves for driving the needle or other tool in the present invention, those skilled in the art will understand that there is a device known generally as a Hartmann generator wherein gas is passed through a nozzle, the nozzle being sufficiently constricted that gas exits from the nozzle at supersonic velocity. This gas then engages a cup coaxially located a short distance beyond the nozzle. In this arrangement, the cup is caused to vibrate at an ultrasonic rate. It will therefore be understood by those skilled in the art that the arrangement for generating the ultrasonic waves utilizes the principle of the Hartmann generator. The Hartmann Generator is described in Ultrasonic Technology, a book written by Richard Goldman and published by Rhienholt Publishing, New York, N.Y. (1962); and in numerous references cited therein, including U.S. Pat. No. 2,800,100.

From the foregoing description, it will be understood that the nozzle 32 is fixed with respect to the body 20. The cup carrying member 30 is held within the bore 29, but the member 30 is movable with respect to the body 20. It will be seen that a plurality of O-rings 42 seals the member 30 with respect to the bore 29 while leaving the member 30 free to move to some extent.

FIG. 4 of the drawings shows more clearly that the nozzle 32 includes a large central passage 44 with an end constriction 45. Gas will exit from the constriction 45 and be directed into the cup 46. Since the cup 46 is open only at the end as shown, it will be understood that the gas from the nozzle 32 will exit from the cup, and pass through the opening 48.

The body of the nozzle 32 is here shown as threadedly received within the sleeve 57. Those skilled in the art will understand that the frequency of vibration in the ultrasonic generator disclosed varies in accordance with the distance between the end of the constriction 45 and the cup 46. As a result, by having the nozzle 32 threadedly carried by the sleeve 57, rotation of the nozzle 32 will vary the distance from the cup 46 to allow the user to tune the device for the desired frequency. It will also be understood that sub-sonic fluid velocities may be used for lower frequencies that will be desirable for some functions.

Attention is next directed to FIG. 5 of the drawings for a better understanding of the fluid circuits in the device, and the mechanical arrangement of the probe end of the handpiece 10. FIG. 5 is a cross-sectional view, but taken in a plane rotated 90° from the drawing in FIG. 2. FIG. 5 therefore shows the passageways 40 and 41. It will be seen that the passageway 41 extends completely through the body 20 and includes an opening 50 leading into the enlarged end 22 of the probe 11. Irrigating fluid can therefore pass through the passageway 41 and into the probe 11. Since the needle 25 is somewhat smaller than the central passage 24 through the probe 11, it will be understood that the irrigation liquid can pass around the needle 25, through the probe 11, and out the tip at 51.

The passageway 40 also extends through the body 20, and is connected into the bore 26. Since the passageway 40 is connected to a source of vacuum, it will be understood that the bore 26 will have the vacuum applied thereto. It will be seen that the stem 31 includes a central passage 52 opening at 54 into the bore 26. The passage 52 extends through the driving member 28, where the passage 52 is placed into communication with the lumen 55 through the needle 25. Thus, the vacuum is available at the tip of the needle 25 for aspirating tissue or the like.

It will be seen that the driving member 28 is provided with an O-ring 56 to seal the vacuum in the bore 26 from the irrigation liquid in the housing 22 of the probe 11.

From the foregoing discussion, it should now be understood that the handpiece of the present invention provides a highly ingenious and useable surgical handpiece that can be operated by fluid alone. For ophthalmic surgery, the incision can be made into the eye, and the probe 11 inserted. Operation of the ultrasonic generator will cause vibration of the member 30, the reciprocation being mechanically passed through the stem 31 to the driving member 28, then to the needle or other tool 25. The needle 25 can be used, for example, to break up a lens for removal. Irrigation liquid can be provided through the passageway 41, and through the passage 24 in the probe 11. This liquid replaces the volume removed from the eye to maintain a balanced pressure, and the liquid also passes between the reciprocating needle 25 and the probe 11 to prevent the buildup of heat due to friction.

The fragmented lens or the like can be aspirated through the lumen 55 in the needle 25, and the material will pass through the passage 52 and into the bore 26, thence through the passageway 40 and through the tubing 15.

It will be seen that the probe 11 is threadedly carried by the body 20, and the needle 25 is threadedly carried by the driving member 28, so these pieces can be replaced so the sizes, or indeed the tool itself, can be exchanged for various procedures.

While those skilled in the art will provide the precise design for the intended instrument, one design for use in ophthalmic surgery requires a gas pressure on the nozzle 32 in the range of 15 to 30 psi. The diameter of the orifice 45 may be approximately 1.5 mm., with the diameter of the cup 46 around 2.2 mm. The ratio of the diameter of the orifice to the diameter of the cup should be maintained to be approximately 1:1.5, and the depth of the cup 46 should be approximately 2.2 mm.

With the dimensions set forth, it will be understood that the rate of vibration of the member 30 will be in the vicinity of 30 to 50 khz., and the reciprocation of the needle 25 or other tool will be through a distance of approximately 0.05 mm.

It will also be readily understood by those skilled in the art that the handpiece herein disclosed is readily adaptable to procedures other than ophthalmic surgery. By way of example, the handpiece 10 can be used to provide an ultrasonically vibrated knife by replacing the needle 25 with a surgical knife. Dental prophylaxis equipment could be made by replacing the needle 25 with a curette of the desired design. A dental drill could be provided by using a solid tool in place of the needle 25, and using the device in conjunction with an abrasive slurry to grind away tooth enamel. A similar tool could be used as an impact hammer for packing amalgam. Numerous other modifications will suggest themselves to those skilled in the art.

It will therefore be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as defined in the appended claims.

I claim:

1. A pneumatically operated surgical handpiece adapted for ultrasonic frequency operation, said surgical handpiece comprising:

a cylindrical body having a first end portion, a middle portion and a second end portion, said body defining an axial first bore within said first end portion, an axial middle bore within said middle portion, and a second axial bore within said second end portion, said bores being axially aligned and provided with interconnections;

a probe member being provided with a first end and an enlarged second end and defining a central axial passageway therethrough for communication with said first bore, said enlarged end of said probe member being releasably attached to said first end portion of said body;

a tool driving member reciprocally positioned within said first bore of said body;

a tool reciprocally positioned within said axial passageway in said probe member, said tool having a first end releasably attached to said tool driving member and a second end extending from said first end of said probe member;

a cylindrical cup carrying member reciprocally positioned within said middle bore of said body, said cup carrying member provided with a centrally disposed cup recess in an end toward said second bore;

a stem connecting said cup carrying member with said tool driving means, said stem passing through said interconnection between said first bore and said middle bore whereby movement of said cup carrying member is transmitted to said tool driving member and to said tool;

a centrally disposed sleeve within said second bore of said body and spaced from walls of said second bore by web means thereby defining gas discharge passageways external to said sleeve; and a nozzle member mounted within said sleeve and provided with means for axial adjustment, said nozzle member having an axial passageway terminating at a first end toward said cup carrying member in a constricted orifice aligned with said cup and at a second end with a means for connecting said passageway of said nozzle member with a source of pressurized gas, said orifice being of a size to produce ultrasonic vibrations upon passage of gas from said source of pressurized gas;

said orifice of said nozzle member and said cup of said cup carrying member being of a selected size and of a selected spacing to form an ultrasonic whistle whereby flow of gas from said source of pressurized gas through said orifice establishes ultrasonic frequencies in said whistle thereby reciprocating said cup carrying member, said tool driving member and said tool at ultrasonic frequencies.

2. The handpiece of claim 2 wherein said means for axial adjustment of said nozzle member comprises providing threads on the inner surface of said sleeve and cooperating threads on the exterior of said nozzle member whereby rotation of said nozzle member effects axial movement of said nozzle member and thus spacing between said orifice and said cup for selecting a selected frequency of reciprocation of said tool.

3. The handpiece of claim 1 wherein:

said tool is provided with an axial lumen;

said tool driving member and said stem are provided with aligned passageways communicating with said lumen;

said stem is provided with a radial opening communicating with said first bore and said axial passageway of said stem; and said body is provided with a first body passageway extending from said second end to proximate said first end of said body, said first body passageway having a first end communicating with said first bore, and a second end at said second end of said body for connection to a vacuum system whereby a vacuum can be applied to said lumen for aspiration through said lumen.

4. The handpiece of claim 1 wherein:

said probe member defines an internal volume, said volume including a concentric space between said probe member and said tool; and said body is provided with a second body passageway extending from said second end to proximate said first end of said body, said second body passageway having a first end communicating with said volume within said probe member, and a second end at said second end of said body for connection to a liquid supply system whereby a liquid can be supplied through said concentric space between said probe member and said tool for irrigation.

5. The handpiece of claim 1 further comprising annular sealing means on said cup carrying member to seal between said cup carrying member and said middle bore during reciprocation against passage of gas from said second bore.

6. The handpiece of claim 1 further comprising annular sealing means on said tool driving member to seal between said tool driving member and said first bore during reciprocation.

7. The handpiece of claim 1 wherein said first end of said tool is threadably attached to said tool driving member whereby said tool can be removed from said handpiece.

8. The handpiece of claim 1 wherein:

said tool is provided with an axial lumen;

said tool driving member and said stem are provided with aligned passageways communicating with said lumen;

said stem is provided with a radial opening communicating with said first bore and said axial passageway of said stem;

said body is provided with a first body passageway extending from said second end of said body to proximate said first end of said body, said first body passageway having a first end communicating with said first bore, and a second end at said second end of said body for connection to a vacuum system whereby a vacuum can be applied to said lumen for asppiration through said lumen;

said probe member defines an internal volume, said volume including a concentric space between said probe member and said tool;

said body is provided with a second body passageway extending from said second end of said body to proximate said first end of said body, said second body passageway having a first end communicating with said volume within said probe member, and a second end at said second end of said body for connection to a liquid supply system whereby a liquid can be supplied through said concentric space between said probe member and said tool for irrigation; and further comprises a control unit interposed between said source of pressurized gas and said second end of said nozzle member, between said vacuum system and said second end of said first body passageway, and between said liquid supply and said second end of said second body passageway said source of pressurized gas, said vacuum system and said liquid supply are selectively connected to said body for operation of said reciprocation, said aspiration and said irrigation, respectively.

9. The handpiece of claim 8 wherein said control unit provides for adjustment of pressure of gas applied to said nozzle member for selecting the reciprocation frequency of said tool.

10. The handpiece of claim 1 wherein said source of pressurized gas provides a pressure of about 15 to 30 psi to said nozzle member, said orifice is circular and has a diameter of about 1.5 mm, said cup is cylindrical and has a diameter of about 2.2 mm and a depth of about 2.2 mm thereby producing an ultrasonic frequency of about 30 to 50 kilohertz with a reciprocation distance of said tool of about 0.05 mm.

11. A pneumatically operated handpiece system for ophthalmic surgery, which comprises:

a cylindrical body having a first end portion, a middle portion and a second end portion, said body defining an axial first bore within said first end portion, an axial middle bore within said middle portion, and a second axial bore within said second end portion, said bores having interconnections, said body further provided with a first body passageway extending from a first end at said first end portion of said body to a second end at said second end portion of said body, and with a second passageway having a first end communicating with said first bore and a second end at said second end portion of said body;

a probe member being provided with a first end and an enlarged end, and defining a central axial passageway therethrough communicating with said first bore and said first body passageway, said enlarged end of said probe member being threadably received by said first end portion of said body and defining an interior volume communicating with said first end of said first body passageway;

a tool driving member reciprocatably positioned within said first bore of said body, said tool driving member provided with an axial passageway;

a tool reciprocally positioned within said axial passageway in said probe member, said tool having a first end threadably attached to said tool driving member and a second end defining a needle extending from said first end of said probe member, said tool provided with an axial lumen communicating with said passageway in said tool driving member;

a cylindrical cup carrying member reciprocally positioned within said middle bore of said body, said cup carrying member provided with a centrally disposed cup recess in an end toward said second bore;

a stem connecting said cup carrying member with said tool driving means, said stem passing through said interconnection between said first bore and said middle bore and provided with an axial passageway communicating with said axial passageway of said tool driving member and with said first bore, said stem transmitting movement of said cup carrying member to said tool driving member and to said tool;

a centrally disposed sleeve within said second bore of said body and spaced from the inner wall of said second bore by web means thereby defining gas discharge passageways external to said sleeve, said sleeve provided with internal threads;

a nozzle member mounted within said sleeve and having external threads cooperating with said threads of said sleeve to provide for axial adjustment of said nozzle member, said nozzle member having an axial passageway terminating at a first end toward said cup carrying member in a constricted orifice axially aligned with said cup, and at a second end with means for connecting said passageway of said nozzle member with a source of pressurized gas, said orifice being of a size to produce ultrasonic vibrations upon passage of gas from said source of pressurized gas, said orifice and said cup being of a selected size and spaced a selected distance to form an ultrasonic whistle whereby flow of said gas from said source of pressurized fluid establishes ultrasonic frequencies in said whistle thereby reciprocating said tool at ultrasonic frequencies;

a source of vacuum;

a source of liquid; and control means for selectively connecting said source of vacuum to said second end of said first body passageway for aspiration through said first bore, said passageway in said stem and in said tool driving member and said lumen of said tool, said control means also for selectively connecting said source of liquid to said second end of said second body passageway for irrigation through said volume within said probe member exterior to said tool, and said control means also for selectively connecting said source of pressurized gas to said second end of said passageway of said nozzle member for ultrasonic reciprocation of said tool.

12. A surgical handpiece adapted for ultrasonic frequency operation, said surgical handpiece comprising:

a cylindrical body having a first end portion, a middle portion and a second end portion, said body defining an axial first bore within said first end portion, an axial middle bore within said middle portion, and a second axial bore within said second end portion, said bores provided with interconnections;

a probe member being provided with a first end and an enlarged second end and defining a central axial passageway therethrough for communication with said first bore, said enlarged end of said probe member being releasably attached to said first end portion of said body;

a tool driving member reciprocally positioned within said first bore of said body;

a tool reciprocally positioned within said axial passageway in said probe member, said tool having a first end releasably attached to said tool driving member and a second end extending from said first end of said probe member;

a cylindrical cup carrying member reciprocatably positioned within said middle bore of said body, said cup carrying member provided with a centrally disposed cup recess in an end toward said second bore;

a stem connecting said cup carrying member with said tool driving means, said stem passing through said interconnection between said first bore and said middle bore whereby movement of said cup carrying member is transmitted to said tool driving member and to said tool;

a centrally disposed sleeve within said second bore of said body and spaced from walls of said second bore by web means thereby defining gas discharge passageways external to said sleeve;

a nozzle member mounted within said sleeve and provided with means for axial adjustment, said nozzle member having an axial passageway terminating at a first end toward said cup carrying member in a constricted orifice aligned with said cup and at a second end with a means for connecting said passageway of said nozzle member with a source of pressurized fluid, said orifice being of a size to produce ultrasonic vibrations upon passage of fluid from said source of pressurized fluid; and said orifice of said nozzle member and said cup of said cup carrying member being of a selected size and of a selected spacing to form an ultrasonic whistle whereby flow of fluid from said source of pressurized fluid through said orifice establishes ultrasonic frequencies in said whistle thereby reciprocating said cup carrying member, said tool driving member and said tool at ultrasonic frequencies.

* * * * *